United States Patent [19]

Bauer et al.

[11] 4,435,385
[45] Mar. 6, 1984

[54] N-ACYL-POLYPEPTIDES AND PROCESSES FOR THE PRODUCTION THEREOF

[75] Inventors: Wilfried Bauer, Lampenberg; Janos Pless, Basel, both of Switzerland

[73] Assignee: Sandoz Ltd., Basel, Switzerland

[21] Appl. No.: 353,900

[22] Filed: Mar. 2, 1982

[30] Foreign Application Priority Data

Mar. 6, 1981 [CH] Switzerland ............... 1531/81
Sep. 4, 1981 [CH] Switzerland ............... 5723/81

[51] Int. Cl.³ .................... A61K 37/00; C07C 103/52
[52] U.S. Cl. ........................... 424/177; 260/112.5 S
[58] Field of Search ................. 260/112.5 S; 424/177

[56] References Cited

U.S. PATENT DOCUMENTS 3,904,594 9/1975 Guillemin et al. ........... 260/112.5 S
4,282,143 8/1981 Sarantakis ................... 260/112.5 S Primary Examiner—Delbert R. Phillips
Attorney, Agent, or Firm—Gerald D. Sharkin; Robert S. Honor; Thomas O. McGovern

[57] ABSTRACT

N-Acyl-polypeptides comprising the basic sequence

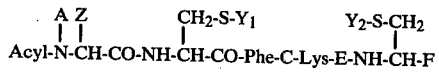

wherein "Acyl" is the acyl residue of an organic or inorganic acid; A is H or alkyl; $>$N—CH(Z)—CO— and E are the residues of natural α-amino acids or corresponding (D)-amino acids; C is —Trp— or —(D)Trp—; F is a terminal grouping; and $Y_1$ and $Y_2$ are each H or together are a direct bond; as well as their salt forms and complexes.

20 Claims, No Drawings

N-ACYL-POLYPEPTIDES AND PROCESSES FOR THE PRODUCTION THEREOF

The present invention relates to novel N-acyl-polypeptides, processes for their production, pharmaceutical compositions comprising said N-acyl-polypeptides and their use as pharmaceutically active agents.

More particularly the present invention relates to N-acyl-polypeptides of formula I,

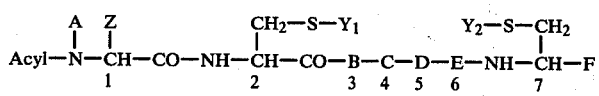

wherein
"Acyl" is the acyl residue of an organic or inorganic acid,
A is hydrogen or $C_{1-3}$alkyl,
$>N-CH(Z)-CO-$ is
(a) an (L)- or (D)-phenylalanine residue optionally ring-substituted by halogen, $NO_2$, $NH_2$, OH, $C_{1-3}$alkyl and/or $C_{1-3}$alkoxy, or
(b) the residue of a natural α-amino acid other than defined under (a) above, or of a corresponding (D)-amino acid,
whereby Z in $>N-CH(Z)-CO-$ represents the remainder of said residue (a) or (b),
B is —Phe— optionally ring-substituted by halogen, $NO_2$, $NH_2$, OH, $C_{1-3}$alkyl and/or $C_{1-3}$alkoxy,
C is —Trp— or (D)-Trp- optionally α-N-methylated and optionally benzene-ring-substituted by halogen, $NO_2$, $NH_2$, OH, $C_{1-3}$alkyl and/or $C_{1-3}$alkoxy,
D is —Lys— optionally α-N-methylated and optionally ε—N—$C_{1-3}$alkylated,
E is the residue of a natural α-amino acid or of a corresponding (D)-amino acid, said residue being optionally α-N-methylated,
F is a group of formula $-COOR_1$, $-CH_2OR_2$,

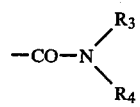

or

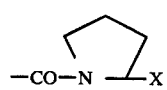

wherein
$R_1$ is hydrogen or $C_{1-3}$alkyl,
$R_2$ is hydrogen or the residue of a physiologically acceptable, physiologically hydrolysable ester,
$R_3$ is hydrogen, $C_{1-3}$alkyl, phenyl or $C_{7-10}$phenylalkyl,
$R_4$ is hydrogen, $C_{1-3}$alkyl or, when $R_3$ is hydrogen or methyl, also a group of formula $-CH(R_5)-X$,
$R_5$ is hydrogen, $-(CH_2)_2-OH$ or $-(CH_2)_3-OH$, or represents the substituent attaching to the α-carbon atom of a natural α-amino acid and
X is a group of formula $-COOR_1$, $-CH_2OR_2$ or

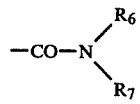

wherein
$R_1$ and $R_2$ have the meanings given above,
$R_6$ is hydrogen or $C_{1-3}$alkyl and
$R_7$ is hydrogen, $C_{1-3}$alkyl, phenyl or $C_{7-10}$phenylalkyl,
the group $-CH(R_5)-X$ having the (D)- or (L)-configuration, and
$Y_1$ and $Y_2$ are each hydrogen or together represent a direct bond,
whereby the residues in the 2- and 7-position each independently have the (L)- or (D)-configuration, and with the proviso that:
(i) (L)- and/or (D)-cysteine residues are present at the 2- and 7-positions only, and
(ii) "Acyl" may not represent a residue $>N-CH(Z)-CO-$ as defined above, in which the α-amino group is unsubstituted or in mono- or di-$C_{1-12}$alkyl substituted,
as well as the salt forms and complexes thereof.

Throughout the present specification and claims by "halogen" is meant fluorine, chlorine and bromine. In accordance with conventional practice, amino acid residues referred to by abbreviation, e.g. —Phe—, —Cys— etc., are to be understood as having the (L)-configuration unless otherwise indicated.

Acyl residues as "Acyl" include, in particular, the acyl residues of organic carboxylic acids, sulfonic acids, sulfaminic acids and carbonic acids and their derivatives. Suitable acyl residues are, e.g. the groups:
1. $R^I CO-$ wherein $R^I$ is an aliphatic, cycloaliphatic, aromatic or heterocyclic group, especially $C_{1-20}$alkyl, $C_{3-20}$alkenyl, $C_{3-20}$alkinyl, phenyl, naphthyl or $C_{7-10}$(phenylalkyl);
2. $R^{II}SO_2-$ wherein $R^{II}$ is $C_{1-10}$alkyl, phenyl or $C_{7-10}$(phenylalkyl);
3. $R^{III}O-CO-$ wherein $R^{III}$ is $C_{1-10}$alkyl or $C_{7-10}$(phenylalkyl); and

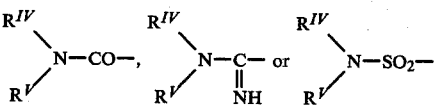

wherein
$R^{IV}$ is hydrogen, $C_{1-10}$alkyl, phenyl or $C_{7-10}$(phenylalkyl) and
$R^V$ is hydrogen or $C_{1-10}$alkyl.

Aliphatic groups as $R^I$ may be saturated or unsaturated, branched- or straight-chain. Similarly alkyl, alkenyl and alkinyl groups as well as the alkyl-moieties of phenylalkyl groups recited as $R^I$ through $R^V$ may all be branched- or straight-chain. All groups recited as $R^I$ through $R^V$ may optionally bear further substituents. Suitably groups recited as $R^I$ through $R^V$ are unsubstituted.

In the N-acyl-polypeptides of formula I, the following significances or combinations thereof are preferred:

5. "Acyl" is a group $R^I CO-$ or $R^{II}SO_2-$ as defined under 1. and 2. above. Most preferably "Acyl" is a group $R^I CO-$.

5.1 When "Acyl" is a group $R^I CO-$, $R^I$ is preferably $C_{1-15}$alkyl, phenyl or $C_{7-10}$(phenylalkyl), more especially $C_{1-15}$alkyl.

5.2 When "Acyl" is a group $R^{II}SO_2-$, $R^{II}$ is preferably $C_{1-10}$alkyl or phenyl optionally substituted by $C_{1-3}$alkyl, especially phenyl or mono- or di-$C_{1-3}$alkyl-substituted phenyl. Most preferably $R^{II}$ is $C_{1-10}$alkyl.

6. A is hydrogen or methyl, especially hydrogen.

7.1 When $>N-CH(Z)-CO-$ has the meaning (a), it is preferably an (L)- or (D)-phenylalanine or (L)- or (D)-tyrosine residue (whereby Z is benzyl or p-OH-benzyl), most preferably a (D)-phenylalanine residue.

7.2 When $>N-CH(Z)-CO-$ has the meaning (b), the defined residue is preferably lipophilic. Preferred residues (b) are accordingly residues in which Z is alkyl having 3, preferably 4, or more carbon atoms, in particular one (L)- or (D)-leucine and (L)- or (D)-nor-leucine residues (in which case Z is iso- and n-butyl respectively).

7.3 Most preferably $>N-CH(Z)-CO-$ has the meaning (a).

8. B is —Phe—.
9. C is —(D)Trp—.
10. D is —Lys— or —MeLys—, especially —Lys—.
11. E is the residue of a natural α-amino acid, especially —Thr—.
12. F is a group of formula

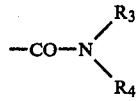

especially a group of formula

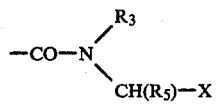

(in which case $R_3=H$ or $CH_3$). In the latter case the moiety $-CH(R_5)-X$ preferably has the L-configuration.

12.1 $R_3$ is preferably hydrogen.

12.2 As the substituent attaching to the α-carbon atom of a natural amino acid (i.e. of formula $H_2N-CH(R_5)-COOH$), $R_5$ is preferably $-CH_2OH$, $-CH(CH_3)-OH$, isobutyl or benzyl, or $R_5$ is $-(CH_2)_2-OH$ or $-(CH_2)_3OH$. It is especially $-CH_2OH$ or $-CH(CH_3)OH$.

12.3 X is preferably a group of formula

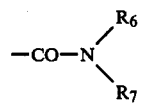

or $-CH_2-OR_2$, especially of formula $-CH_2OR_2$ and $R_2$ is preferably hydrogen or has the meaning given under 13. below. Most preferably it is hydrogen.

13. As the residue of a physiologically acceptable, physiologically hydrolysable ester $R_2$ is preferably HCO, $C_{2-12}$-alkylcarbonyl, $C_{8-12}$phenylalkylcarbonyl or benzoyl.

14. Preferably the residues in the 2- and 7-positions have the (L)-configuration.

15. Preferably $Y_1$ and $Y_2$ together represent a direct bond.

A particularly interesting group of N-acyl-polypeptides of formula I are those wherein "Acyl" represents an acyl residue incorporating an aliphatic moiety (e.g. as $R^I$, $R^{II}$, $R^{III}$ or $R^{IV}$ of the groups defined under 1. to 4. above) having at least 7, preferably at least 8 carbon atoms, compounds of this type (hereinafter referred to as "N-acyl-polypeptides of Type-T") being characterised by a more prolonged duration of activity when administered sub-cutaneously. Preferred N-acyl-polypeptides of Type-T are those wherein "Acyl" is a group $R^I CO-$ or $R^{II}SO_2-$, especially a group $R^I CO-$, wherein $R^I$ is $C_{7-15}$alkyl, preferably $C_{7-10}$alkyl, especially $C_{8-15}$alkyl, preferably $C_{8-10}$alkyl, and $R^{II}$ is $C_{7-10}$alkyl, especially $C_{8-10}$alkyl. Especially preferred are N-acyl-polypeptides of Type-T, wherein the remaining residues in formula I have the significances specified under (6.) through (15.) above.

The N-acyl-polypeptides of the invention may exist in salt form or in the form of complexes thereof. Acid addition salts may be formed with e.g. organic acids, polymeric acids and inorganic acids. Such acid addition salt forms include e.g. the hydrochlorides and acetates. By complexes are to be understood compounds of known type, formed from compounds of formula I on addition of inorganic substances, e.g. inorganic salts or hydroxides such as Ca- and Zn-salts, and/or on addition of polymeric organic substances.

The present invention also provides a process for the production of the compounds according to the invention. These compounds may be produced by methods known in the art of peptide chemistry or by obvious chemical equivalents thereof, for example by a process comprising:

(a) removing the protecting group or groups from a protected N-acyl-polypeptide having the sequence indicated in formula I, (b) linking together by an amide bond two peptide units, each of which contains at least one amino acid or amino alcohol residue in protected or unprotected form, the peptide units being such that a protected or unprotected N-acyl-polypeptide having the sequence indicated in formula I is obtained and, if necessary, carrying out process step (a);

(c) converting the group F of a protected or unprotected N-acyl-polypeptide having the sequence indicated in formula I, into another group F, and, if necessary carrying out process step (a);

(d) oxidising an N-acyl-polypeptide of formula I wherein $Y_1$ and $Y_2$ are each hydrogen to provide an N-acyl-polypeptide of formula I, wherein $Y_1$ and $V_2$ together are a direct bond, and recovering the N-acyl-polypeptide thus obtained in free or salt form or as a complex thereof.

The above process may for example be carried out analogously to the processes described in the accompanying examples. Insofar as the production of the starting materials is not particularly described, the compounds are known or may be produced and purified in accordance with methods known in the art. In the following examples $[\alpha]_D^{20}$ values are uncorrected. The following abbreviations are employed:

AcOH = acetic acid
AcOEt = ethyl acetate
BOC = tert.-butoxycarbonyl
BTFA = boron-tris-trifluoroacetate
DCCI = dicyclohexylcarbodiimide
DMF = N,N-dimethylformamide
HOBT = N-hydroxybenzotriazole
Leu-ol = the leucinol residue

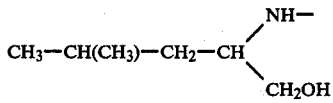

MBzl = p-methoxybenzyl
Me = methyl
MeOH = methanol
NEt₃ = triethylamine
ONP = 4-Nitrophenoxy
Phe(pNO₂) = p-NO₂-Phenylalanine
TFA = trifluoroacetic acid
THF = tetrahydrofuran
Thr-ol = the threoninol residue

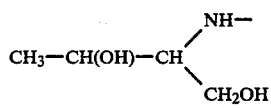

Z = benzyloxycarbonyl

EXAMPLE 1

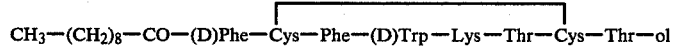

7.1 g CH₃-(CH₂)₈-CO-(D)Phe-Cys-(MBzl)-Phe-(D)Trp-Lys(Z)-Thr-Cys-(MBzl)-Thr-ol and 54 ml thioanisole are dissolved in 120 ml TFA at 0° C. The solution is cooled to −10° C., 92 ml ca. 2M BTFA in TFA are added and the solution is stirred for 1.5 hrs. at −10° to −5° C. The obtained reaction mixture is then added with stirring to 400 ml abs. MeOH at −70° C. and stirred after 5 minutes with a mixture of 20 ml HCl/ethyl-ether (~5 N) in 9 liters absolute ethyl-ether.

The precipitated product is filtered off, washed with ethyl ether and dissolved immediately in 16 liters of dioxane/H₂O (7:3). 4 N NH₄OH is added with stirring until the pH reaches 7 to 7.5 and the solution is stirred in an open vessel until testing for —SH groups (e.g. by the Ellmann-method) is negative.

The pH is adjusted to ~3 to 4 by addition of dilute HCl, the solution concentrated under vacuum and lyophylised. The raw product is purified chromatographically on silica gel using a mixture of CHCl₃/MeOH/AcOH/H₂O as eluant. Fractions containing the desired product are combined, diluted with H₂O, concentrated and lyophylised to yield the title compound in pure form:

$[\alpha]_D^{20} = -43.7°$ (c = 0.92 in 95% AcOH). The starting material is produced as follows:

(a) BOC-Cys(MBzl)-Thr-ol 2.1 ml N-methylmorpholine are added with stirring to a solution of 6.3 g Boc-Cys(MBzl)-OH in 50 ml THF, followed by drop-wise addition at −15° C. of 2.4 ml chloroformic acid isobutyl ester. After stirring for 5 minutes at −15° C. a solution of 3.3 g H-Thr-ol hydrochloride and 4.1 ml N-methylmorpholine in 30 ml DMF, pre-cooled to −10° C. is added. The reaction mixture is stirred for 2 hrs. at 0° C. and for a further 2 hrs. at room-temperature. 50 ml 10% KHCO₃-solution are added and the whole concentrated under vacuum. After dilution with AcOEt, washing 3× with 2 N citric acid, 3× with KHCO₃-solution and 1× with NaCl solution, the organic phase is dried over Na₂SO₄ and evaporated under vacuum to yield the title compound:
$[\alpha]_D^{20} = -31°$ (c = 1.3 in DMF).

(b) H-Cys(MBzl)-Thr-ol trifluoroacetate 7.1 g BOC-Cys(MBzl)-Thr-ol and 5 ml thioanisole are dissolved in 25 ml methylene chloride. The solution is added to 50 ml TFA and allowed to stand for 20 minutes at room temperature. The mixture is diluted with ca. 1.5 liters ethyl-ether and the precipitated product filtered off and dried to yield the title compound:
$[\alpha]_D^{20} = 8.3$ (c = 1.1 in 95% AcOH); M.P. = 152° C.

(c) BOC-Thr-Cys(MBzl)-Thr-ol 5.9 ml chloroformic acid isobutyl-ester are added drop-wise to a solution of 9.7 g Boc-Thr-OH and 9.4 ml N-methyl-morpholine in 50 ml THF pre-cooled to −25° C. The solution is stirred for 5 min. at −15° C. and a solution of 20 g H-Cys(MBzl)-Thr-ol trifluoroacetate and 9.8 ml N-methylmorpholine in 50 ml THF, pre-cooled to −10° C. are added. The reaction mixture is stirred for 2 hrs. at 0° C., and for 2 hrs. at room temperature. 20 ml 10% KHCO₃ are added and the mixture concentrated under vacuum. The product is diluted with AcOEt and washed with 2 N citric acid, 10% KHCO₃ solution and then 30% NaCl solution. The AcOEt phase is dried over Na₂SO₄ and evaporated under vacuum, and the residue re-crystallised from MeOH/AcOEt/hexane. The title compound is obtained after further filtration, washing with ether and drying:
$[\alpha]_D^{20} = -23°$ (c = 1 in DMF); M.P. = 117° C.

(d) H-Thr-Cys(MBzl)-Thr-ol trifluoroacetate 150 ml TFA are added to a solution of 16 g BOC-Thr-Cys(MBzl)-Thr-ol and 17 ml thioanisole in 100 ml methylene chloride pre-cooled to 0° C. The whole is allowed to stand for 20 minutes at room temperature and stirred into ethyl-ether. The precipitated product is filtered off, washed with ethyl-ether and dried to yield the title compound:
$[\alpha]_D^{20} = +0.6°$ (c = 1 in 95% AcOH); M.P. = 72° C.

(e) BOC-(D)Trp-Lys(Z)-OMe 9.8 ml NEt₃, 11.8 g HOBT and 21.3 g BOC-(D)Trp-OH are added to 23.3 g H-Lys(Z)-OMe hydrochloride in 300 ml DMF, and the solution cooled to −15° C. 15.6 g DDCI in 50 ml DMF are added and the reaction mixture stirred for ca. 16 hrs. at 0° C., followed by 2 hrs. at room temperature. The reaction mixture is diluted with AcOEt/ethyl-ether and the dicyclohexyl-urea is filtered off. The filtrate is washed with 2 N citric acid, H$_2$O, 10% KHCO$_3$ solution and 30% NaCl solution. The organic phase is dried over Na$_2$SO$_4$ and concentrated strongly under vacuum. Crystallisation is effected by the addition of ethyl-ether/hexane and the product is filtered off, washed with ethyl-ether/hexane and dried to yield the title compound:

$[\alpha]_D^{20} = -12.6°$ (c=1 in DMF); M.P.=140° C.

(f) H-(D)Trp-Lys(Z)-OMe hydrochloride 150 ml TFA are added to 30 g BOC-(D)Trp-Lys(Z)-OMe in 150 ml methylene chloride pre-cooled to 0° C. The whole is stirred for 40 minutes at room-temperature and then added to 30 ml HCl/ethyl-ether (~5 N) in 4 l ethyl-ether. After thorough stirring the precipitate is filtered off, washed with ethyl-ether and dried to yield the title compound:

$[\alpha]_D^{20} = -44°$ (c=1 in 95% AcOH); M.P.=101° C.

(g) BOC-Phe-(D)Trp-Lys(Z)-OMe 9.5 ml NEt$_3$, 13 g HOBT and 17 g BOC-Phe-OH are added to 35 g H-(D)Trp-Lys(Z)-OMe hydrochloride in 350 ml DMF. The solution is cooled to −20° C. and 14.5 g DCCI dissolved in 50 ml DMF are added. The reaction mixture is stirred for ca. 18 hrs. at 0° C. and then for 1 day at room temperature. The precipitated dicyclohexyl-urea is filtered off and the filtrate is concentrated, diluted with methanol and H$_2$O added until precipitation occurs. After filtration the residue is washed with MeOH/H$_2$O (4:1) and dried to yield the title compound:

$[\alpha]_D^{20} = +1.1°$ (c=1 in DMF); M.P.=180° C.

(h) BOC-Phe-(D)Trp-Lys(Z)-OH 26 ml 1 N NaOH are added to a suspension of 16 g BOC-Phe-(D)Trp-Lys(Z)-OMe in dioxane/H$_2$O (8:2) and the reaction mixture stirred for 1.5 hrs. at room temperature. The obtained solution is diluted to ca. 500 ml by the addition of H$_2$O and then concentrated under vacuum. The pH is adjusted to 1.5 to 2 by the addition, with stirring, of 1 N HCl, the precipitated product is filtered off, washed with H$_2$O until neutral and dried to yield the title compound:

$[\alpha]_D^{20} = +7.6°$ (c=1 in DMF); decomposition at 85°-90° C.

(i) BOC-Phe-(D)Trp-Lys(Z)-Thr-Cys(MBzl)-Thr-ol 2.5 ml NEt$_3$, 11.2 g BOC-Phe-(D)Trp-Lys(Z)-OH and 4 g HOBT are added to 9 g H-Thr-Cys(MBzl)-Thr-ol trifluoroacetate in 100 ml DMF. 3.7 g DCCI in 10 ml DMF are added to the solution at −20° C. and the whole is stirred for ca. 18 hours at 0° C. and 2 hrs. at room temperature. Precipitated dicyclohexyl-urea is filtered off and the filtrate concentrated under vacuum and diluted with methanol. H$_2$O is added until the product precipitates. The precipitate is filtered, washed with MeOH/H$_2$O (4:1) and dried to yield the title compound:

$[\alpha]_D^{20} = -14°$ (c=1 in DMF); M.P.=135° C.

(j) H-Phe-(D)Trp-Lys(Z)-Thr-Cys(MBzl)-Thr-ol hydrochloride 13 g BOC-Phe-(D)Trp-Lys(Z)-Thr-Cys(MBzl)-Thr-ol are dissolved in 60 ml cold TFA/H$_2$O (15:1) and the solution allowed to stand for 30 min. at room temperature. The reaction mixture is stirred into a mixture comprising 3 liters ethyl-ether and 20 ml HCl in ethyl-ether (~5 N) and the precipitated product filtered off, washed with ethyl-ether and dried to yield the title compound:

$[\alpha]_D^{20} = -3°$ (c=1 in DMF); decomposition at 110° C.

(k) BOC-(D)Phe-Cys(MBzl)-OH 7.73 g BOC-(D)Phe-ONP are added to a solution of 4.83 g H-Cys-(MBzl)-OH in 100 ml dioxane/H$_2$O (7:3) and 20 ml 1 N NaOH and the obtained reaction mixture is stirred for 20 hrs. at room temperature. The reaction mixture is diluted with H$_2$O and the dioxane removed under vacuum. The aqueous phase is washed with ether and the pH adjusted to 2 by the addition of HCl. The precipitated product is extracted with AcOEt/ethyl-ether, the organic phase washed with water, dried over Na$_2$SO$_4$ and evaporated under vacuum to yield the title compound as a foam:

$[\alpha]_D^{20} = -17°$ (c=0.9 in DMF).

(l) H-(D)Phe-Cys(MBzl)-OH hydrochloride 5 g BOC-(D)Phe-Cys(MBzl)-OH are dissolved in 80 ml TFA and 10 ml H$_2$O and allowed to stand for 45 minutes at room-temperature. The solution is diluted with ethyl-ether and 20 ml ethyl-ether/HCl (~5 N) are added, and the precipitate is filtered off, washed with ethyl ether and dried to yield the title compound:

$[\alpha]_D^{20} = -38.5°$ (c=0.93 in 95% AcOH); M.P.=189° C.

(m) CH$_3$-(CH$_2$)$_8$-CO-(D)Phe-Cys(MBzl)-OH 23.3 ml 1 N NaOH are added to 10.0 g H-(D)Phe-Cys(MBzl)-OH hydrochloride in 100 ml dioxane. 7 ml CH$_3$(CH$_2$)$_8$COCl are then added drop-wise with stirring and with simultaneous addition of 1 N NaOH, whereby the pH is kept at 8. The obtained reaction mixture is then stirred for a further 20 hrs. at room temperature. The reaction mixture is then adjusted to pH 2 by addition of 4 N HCl, concentrated under vacuum, diluted with H$_2$O and extracted with AcOEt. The organic phase is washed with H$_2$O, dried over Na$_2$SO$_4$ and evaporated under vacuum. The residue is purified chromatographically on silica gel using methylene chloride/MeOH as eluant to yield the title compound:

$[\alpha]_D^{20} = -19.3°$ (c=2.6 in DMF). M.P.=124° C.

(n) CH$_3$-(CH$_2$)$_8$-CO-(D)Phe-Cys(MBzl)-Phe-(D)Trp-Lys(Z)-Thr-Cys(MBzl)-Thr-ol 0.7 ml N-methylmorpholine are added to a solution of 5.7 g H-Phe-(D)Trp-Lys(Z)-Thr-Cys(MBzl)-Thr-ol hydrochloride, 0.8 g HOBT and 2.7 g CH$_3$-(CH$_2$)$_8$-CO-(D)Phe-Cys(MBzl)-OH in 60 ml DMF. The solution is cooled to −15° C., 1.20 g DCCI in 10 ml DMF are added, and the reaction mixture stirred for 70 hrs. at 0° to 4° C. Precipitated dicyclohexyl-urea is filtered off, the filtrate diluted with MeOH and H$_2$O added with stirring until the product precipitates. Filtration is effected after ca. 2 hrs., the residue washed with MeOH/H$_2$O (2:1) and dried under vacuum to yield the title compound:

$[\alpha]_D^{20} = -20.5°$ (c=0.8 in DMF).

The following compounds may be produced analogously to the process of example 1 (all compounds listed in the form of the acetate):

| Example No. | Acyl—(D)Phe—Cys—Phe—(D)Trp—Lys—Cys—Thr—ol "Acyl" | $[\alpha]_D^{20}$ in 95% AcOH |
|---|---|---|
| 2 | $CH_3CO-$ | $-42.8°$ (c = 0.5) |
| 3 | $CH_3(CH_2)_4CO-$ | $-35.8°$ (c = 0.53) |
| 4 | $CH_3(CH_2)_6CO-$ | $-34.0°$ (c = 0.40) |
| 5 | $CH_3(CH_2)_7CO-$ | $-35.6°$ (c = 0.69) |
| 6 | $CH_3(CH_2)_{10}CO-$ | $-36.5°$ (c = 0.50) |
| 7 | $CH_3(CH_2)_{12}CO-$ | $-27.3°$ (c = 0.50) |
| 8 | $t.C_4H_9-CO-$ | $-24.0°$ (c = 1.0) |
| 9 | 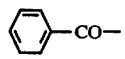 | $-33.0°$ (c = 1.0) |
| 10 | 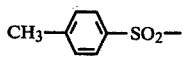 | $-14.3°$ (c = 1.0) |
| 11 | $C_2H_5NH-CO-$ | $-32.2°$ (c = 0.46) |
| 12 | D(+)-Biotinyl | $-16.9°$ (c = 1.0) |
| 13 | $CH_3(CH_2)_9SO_2-$ | $-31.0°$ (c = 0.5) |

| Example No. | Acyl—A—Cys—B—(D)Trp—Lys—Thr—Cys—F "Acyl" | A | B | F |
|---|---|---|---|---|
| 14 | $CH_3(CH_2)_4CO-$ | $-(D)Phe(pNO_2)-$ | $-Phe-$ | $-Thr-ol$ |
| 15 | $CH_3(CH_2)_{10}CO-$ | $-(D)Nle-$ | $-Phe-$ | $-Thr-ol$ |
| 16 | $CH_3(CH_2)_6CO-$ | $-(D)Phe-$ | $-Phe(pNO_2)-$ | $-Thr-ol$ |
| 17 | $CH_3(CH_2)_{12}CO-$ | $-(D)Phe-$ | $-Phe-$ | $-(D)Thr-NH_2$ |
| 18 | $CH_3(CH_2)_{12}CO-$ | $-(D)Phe-$ | $-Phe-$ | $-Phe-OMe$ |
| 19 | $CH_3(CH_2)_{12}CO-$ | $-(D)Phe-$ | $-Phe-$ | $-Leu-ol$ |

EXAMPLE 20

Proceeding analogously to examples 1 through 19, but omitting the final oxidisation step, the straight-chain N-acyl-polypeptides corresponding to each of the individual monocyclic polypeptides recited (i.e. wherein the —Cys— residues in the 2- and 7-positions are not linked) are produced. Thus omitting the final oxidisation step from the process of example 1, there is produced the straight-chain N-acyl-polypeptide of formula, $CH_3$-$(CH_2)_8$-CO-(D)Phe-Cys-Phe-(D)Trp-Lys-Thr-Cys-Thr-ol [acetate]

$[\alpha]_D^{20}$ in 95% AcOH= $-33.8°$; (c=0.42).

N-acyl-polypeptides of the invention as well as their pharmaceutically acceptable salts and complexes exhibit valuable pharmacological properties as indicated in animal tests. In particular they exhibit GH-secretion inhibiting activity as indicated e.g. by depression of serum GH-levels in the rat.

This test (TEST I) is carried out employing male rats under Nembutal narcosis. The test-substance is administered at varying, logarithmically staggered doses employing at least 4 rats per dose. The rats are decapitated 60 minutes after administration, the blood is collected and the serum GH-level determined by radioimmuno-assay.

N-Acyl-polypeptides in accordance with the invention are active in this test when administered at a dosage in the range of from 0.1 to 1000 µg/kg s.c.

The above test may be adapted to determine effectiveness over prolonged periods of time, e.g. by decapitating 6 or 18 hours after administration. N-acyl-polypeptides of Type-T as hereinbefore defined are of especial interest, in that they are active in the above described test method when administered at dosages in the aforesaid range, over prolonged periods of time and up to 18 hours.

The said N-acyl-polypeptides, salts and complexes are accordingly useful in the treatment of disorders with an aetiology comprising or associated with excess GH-secretion, e.g. in the treatment of diabetes mellitus and angiopathy as well as of acromegaly.

The said N-acyl-polypeptides, salts and complexes also inhibit gastric- and pancreatic secretion as indicated in standard animal test, e.g. in accordance with the following method for the measurement of gastric secretion (Test II):

Male rats (220–280 g) are kept in the laboratory in individual cages for several days (14 hours light/day) with 48 hours fasting (but free access to water) immediately prior to the experiment. At the start of the experiment the pylorus is ligated under ether anaesthesia and 100 µg/kg pentagastrin are injected s.c. to stimulate gastric secretion. The test compounds are injected simultaneously i.m. 30 mins. later the animals are sacrificed, the volume of gastric juice measured and the acid concentration estimated (titration with thymol blue). The acid output is calculated and the percent inhibition estimated in relation to untreated controls.

N-Acyl-polypeptides in accordance with the invention are active in this test when administered at a dosage in the range of from 0.1 to 1000 µg/kg i.m.

The said N-acyl-polypeptides, salts and complexes are thus useful in the treatment of gastro-intestinal disorders, for example in the treatment of gastric ulcer, gastro-intestinal bleeding and acute pancreatitis.

The pharmaceutically acceptable salts and complexes of the polypeptides of the invention show activity of the same order as the free compounds in the above described test methods.

For the above uses the dosage will, of course, vary depending on the compound employed, mode of administration and treatment desired. However, in general satisfactory results are obtained when administered at a daily dosage of from about 0.1 µg to about 1.0 mg/kg conveniently given in divided doses 2 to 4 times a day or in sustained release form. For larger mammals, the total daily dosage is in the range of from about 0.01 mg to about 100 mg N-acyl-polypeptide, and suitable unit dosage forms e.g. for parenteral administration contain from about 0.0025 to about 50 mg, of an N-acyl-polypeptide in accordance with the invention or an equivalent amount of a pharmaceutically acceptable salt or complex thereof, together with a solid or liquid pharmaceutical diluent or carrier therefor.

The daily dosages suitable for any particular compound will, of course, depend on a number of factors including relative potency of activity. The preferred compound of the invention is the compound of example 1, namely $$CH_3-(CH_2)_8-CO-(D)Phe-\overline{Cys-Phe-(D)Trp-Lys-Thr-Cys}-Thr-ol.$$

Administered in the form of the acetate, this compound has, for example, been determined to have an $ID_{50}$ in TEST I above of 13.0 µg/kg s.c. for activity at 60 minutes; 16.0 µg/kg s.c. for activity at 6 hours; and 28 µg/kg s.c. for activity at 18 hours, and in TEST II above of 4.5 µg/kg i.m., for gastric juice content and 2.1 µg/kg for acid concentration, the determined $ID_{50}$ being in each case the amount of compound required to effect 50% inhibition for the measured parameter compared with untreated controls. For the known compound somatostatin, determined $ID_{50}$ values are: for TEST I—93 µg/kg s.c. for activity at 60 minutes and for TEST II—55 µg/kg i.m. for gastric juice content and 35 µg/kg i.m. for acid concentration. Thus an indicated daily dosage for the compound of example 1 would be from about 0.5 µg to about 500 µg/kg s.c. for use as a GH secretion inhibitor and from about 0.15 µg to about 150 µg/kg i.m. for use as a gastric or pancreatic secretion inhibitor.

In accordance with the foregoing the present invention further provides:

(1) a method of treating disorders with an aetiology comprising or associated with excess GH-secretion (such as diabetes mellitus, angiopathy and acromegaly) as well as of treating gastro-intestinal disorders (such as gastric ulcer, gastro-intestinal bleeding and acute pancreatitis), in a subject in need of such treatment, which method comprises administering to said subject an effective amount of an N-acyl-polypeptide in accordance with the invention or of a pharmaceutically acceptable salt or complex thereof and (2) pharmaceutical compositions comprising an N-acyl-polypeptide in accordance with the invention or a pharmaceutically acceptable salt or complex thereof, together with a pharmaceutically acceptable diluent or carrier therefor.

We claim:

1. An N-acyl-polypeptide of formula I, $$\begin{array}{c} \phantom{Acyl-N-}A\phantom{-}Z \phantom{-CO-NH-}CH_2S-Y_1 \phantom{-CO-B-C-D-E-NH-}Y_2-S-CH_2 \\ \phantom{Acyl-N-}|\phantom{-}| \phantom{-CO-NH-}| \phantom{-CO-B-C-D-E-NH-}| \\ Acyl-N-CH-CO-NH-CH-CO-B-C-D-E-NH-CH-F \\ \phantom{Acyl-N-}1 \phantom{-CH-CO-NH-}2 \phantom{-CO-B-}3\,4\,5\,6\phantom{-E-NH-}7 \end{array} \quad (I)$$

where

"Acyl" is (a) $R^I CO-$ wherein $R^I$ is $C_{1-20}$alkyl, $C_{3-20}$alkenyl, $C_{3-20}$alkinyl, phenyl, naphthyl or $C_{7-10}$(phenylalkyl);

(b) $R^{II}SO_2-$ wherein $R^{II}$ is $C_{1-10}$alkyl, phenyl or $C_{7-10}$(phenylalkyl);

(c) $R^{III}O-CO-$ wherein $R^{III}$ is $C_{1-10}$alkyl or $C_{7-10}$(phenylalkyl); and (d) $\begin{array}{c}R^{IV}\\ \diagdown\\ \phantom{R^V}N-CO-,\\ \diagup\\ R^V\end{array}$ $\begin{array}{c}R^{IV}\\ \diagdown\\ \phantom{R^V}N-C-\\ \diagup\phantom{-}\|\\ R^V\phantom{-}NH\end{array}$ or $\begin{array}{c}R^{IV}\\ \diagdown\\ \phantom{R^V}N-SO_2-\\ \diagup\\ R^V\end{array}$ wherein $R^{IV}$ is hydrogen, $C_{1-10}$alkyl, phenyl or $C_{7-10}$(phenylalkyl) and $R^V$ is hydrogen or $C_{1-10}$alkyl, A is hydrogen or $C_{1-3}$alkyl, $>N-CH(Z)-CO-$ is (a) an (L)- or (D)-phenylalanine residue optionally ring-substituted by halogen, $NO_2$, $NH_2$, OH, $C_{1-3}$alkyl and/or $C_{1-3}$alkoxy, or (b) the residue of a natural α-amino acid in which Z is alkyl of 3 to 4 carbon atoms, B is —Phe— optionally ring-substituted by halogen, $NO_2$, $NH_2$, OH, $C_{1-3}$alkyl and/or $C_{1-3}$alkoxy, C is —Trp— or (D)-Trp- optionally α-N-methylated and optionally benzene-ring-substituted by halogen, $NO_2$, $NH_2$, OH, $C_{1-3}$alkyl and/or $C_{1-3}$alkoxy, D is —Lys— optionally α-N-methylated and optionally ε-N-$C_{1-3}$alkylated, E is —Thr— or —(D)—Thr— optionally α-N-methylated, F is a group of formula $-COOR_1$, $-CH_2OR_2$, $$-CO-N\begin{array}{c}\diagup R_3\\ \diagdown R_4\end{array}$$

or $$-CO-N\underset{X}{\overset{\frown}{\diagdown}}$$

wherein $R_1$ is hydrogen or $C_{1-3}$alkyl, $R_2$ is hydrogen or the residue of a physiologically acceptable, physiologically hydrolysable ester, $R_3$ is hydrogen or methyl, $R_4$ is $-CH(R_5)-X$, $R_5$ is hydrogen, $-(CH_2)_2-OH$, $-(CH_2)_3-OH$, $-CH_2-OH$, $-CH(CH_3)-OH$ or isobutyl, and X is a group of formula $-COOR_1$, $-CH_2OR_2$ or $$-CO-N\begin{array}{c}\diagup R_6\\ \diagdown R_7\end{array}$$

wherein $R_1$ and $R_2$ are as defined above, $R_6$ is hydrogen or $C_{1-3}$alkyl and $R_7$ is hydrogen, $C_{1-3}$alkyl, phenyl or $C_{7-10}$phenylalkyl, the group $-CH(R_5)-X$ having the (D)- or (L)-configuration, and $Y_1$ and $Y_2$ are each hydrogen or together represent a direct bond, whereby the residues in the 2- and 7-position each independently have the (L)- or (D)-configuration, and with the proviso that (L)- and/or (D)-cysteine residues are present at the 2- and 7-positions only, or a pharmaceutically acceptable salt or complex thereof.

2. An N-acyl-polypeptide according to claim 1, wherein "Acyl" is a group $R^I CO-$ or $R^{II} SO_2-$, wherein $R^I$ is $C_{1-20}$alkyl, $C_{3-20}$alkenyl, $C_{3-20}$alkinyl, phenyl, naphthyl or $C_{7-10}$phenylalkyl; and $R^{II}$ is $C_{1-10}$alkyl, phenyl or $C_{7-10}$(phenylalkyl), or a pharmaceutically acceptable salt or complex thereof.

3. An N-acyl-polypeptide according to claim 2, wherein $R^I$ is $C_{7-15}$alkyl and $R^{II}$ is $C_{7-10}$alkyl, or a pharmaceutically acceptable salt or complex thereof.

4. An N-acyl-polypeptide according to claim 2, wherein "Acyl" is a group $R^I CO-$, or a pharmaceutically acceptable salt or complex thereof.

5. An N-acyl-polypeptide according to claim 1 of formula $CH_3(CH_2)_8\text{-}CO\text{-}(D)Phe\text{-}Cys\text{-}Phe\text{-}(D)Trp\text{-}Lys\text{-}Thr\text{-}Cys\text{-}Thr\text{-}ol$ or a pharmaceutically acceptable salt or complex thereof.

6. A polypeptide according to claim 1 of the formula

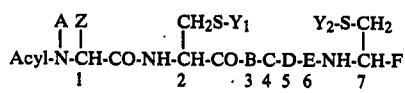

where
"Acyl" is $R^I CO$ or $R^{II} SO_2$;
$R^I$ is $C_{1-15}$alkyl, phenyl or $C_{7-10}$(phenylalkyl);
$R^{II}$ is $C_{1-10}$alkyl or phenyl optionally substituted by $C_{1-3}$alkyl;
A is hydrogen;
$>N-CH(Z)-CO-$ is $-(D)-Phe$ or $-(D)-Nle-$;
B is $-Phe-$;
C is $-(D)-Trp-$;
D is $-Lys-$;
E is $-Thr-$;
F is

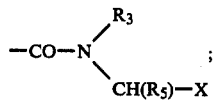

$R_3$ is hydrogen;

$R_5$ is $-CH_2OH$; $-CH(CH_3)OH$ or isobutyl;
X is $-CH_2OR_2$;
$R_2$ is hydrogen and
$Y_1$ and $Y_2$ together represent a direct bond;

or a pharmaceutically acceptable salt or complex thereof.

7. A compound according to claim 1 in which "Acyl" is $R^I CO-$ wherein $R^I$ is $C_{1-15}$alkyl.

8. A compound according to claim 1 in which $>N-CH(Z)-CO-$ is $-(D)-Phe-$.

9. A compound according to claim 1 in which $R_5$ is $-CH_2OH$ or $-CH(CH_3)OH$.

10. The compound according to claim 1 which is

pharmaceutically acceptable salt or complex thereof.

11. A compound according to claim 1 of the formula

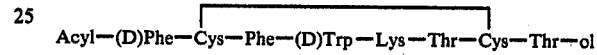

in which Acyl is selected from the group consisting of $CH_3CO$, $CH_3(CH_2)_4CO-$, $CH_3(CH_2)_6CO-$, $CH_3(CH_2)_7CO-$, $CH_3(CH_2)_{10}CO-$, $CH_3(CH_2)_{12}CO-$ and $t.C_4H_9-CO-$ or a pharmaceutically acceptable salt or complex thereof.

12. A compound according to claim 1 of the formula

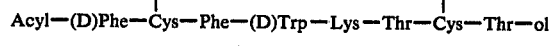

in which Acyl is selected from the group consisting of

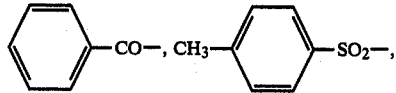

$C_2H_5NH-CO-$, $D(+)$-Biotinyl and $CH_3(CH_2)_9SO_2-$ or a pharmaceutically acceptable salt or complex thereof.

13. The pharmaceutical composition according to claim 10 in which the N-Acyl-polypeptide is

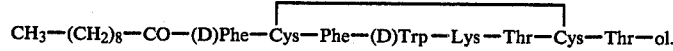

14. The method according to claim 11 in which the N-Acyl-polypeptide is

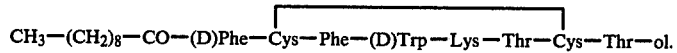

15. The method according to claim 13 in which the N-Acyl-polypeptide is

16. A pharmaceutical composition useful in inhibiting GH secretion and in treating gastrointestinal disorders comprising an effective amount of an N-acyl-polypeptide as defined in claim 1 or a pharmaceutically acceptable salt or complex thereof, together with a pharmaceutically acceptable diluent or carrier therefor.

17. A method of treating disorders with an aetiology comprising or associated with excess GH-secretion, in a subject in need of such treatment, which method comprises administering to said subject an effective amount of an N-acyl-polypeptide as defined in claim 1 or of a pharmaceutically acceptable salt form or complex thereof.

18. A method according to claim 17 for the treatment of diabetes mellitus, angiopathy or acromegaly.

19. A method of treating gastro-intestinal disorders in a subject in need of such treatment, which method comprises administering to said subject an effective amount of an N-acyl-polypeptide as defined in claim 1 or of a pharmaceutically acceptable salt form or complex thereof.

20. A method according to claim 19 for the treatment of gastric ulcer, gastro-intestinal bleeding or acute pancreatitis.

* * * * *